US006350434B1

(12) United States Patent
Bhatt et al.

(10) Patent No.: US 6,350,434 B1
(45) Date of Patent: Feb. 26, 2002

(54) METHOD OF STYLING HAIR WITH HAIR SPRAY COMPOSITIONS CONTAINING CARBOXYLATED POLYURETHANE RESINS

(75) Inventors: Darshna Bhatt, Schaumburg; Ramiro Galleguillos, Glendale Heights, both of IL (US); Ken Nelson, Lambertville; Murray H. Reich, Princeton, both of NJ (US)

(73) Assignee: Helene Curtis, Inc., Chicago, IL (US)

( * ) Notice: Subject to any disclaimer, the term of this patent is extended or adjusted under 35 U.S.C. 154(b) by 0 days.

(21) Appl. No.: 09/437,883

(22) Filed: Nov. 9, 1999

Related U.S. Application Data

(62) Division of application No. 08/717,427, filed on Sep. 20, 1996.
(51) Int. Cl.⁷ .................................................. A61K 7/11
(52) U.S. Cl. ..................... 424/47; 424/45; 424/70.11; 424/78.17; 424/78.37; 424/DIG. 1; 424/DIG. 2; 132/203
(58) Field of Search ...................... 424/45, 47, DIG. 1, 424/DIG. 2, 70.11, 78.17, 78.37; 132/203

(56) References Cited

U.S. PATENT DOCUMENTS

| 4,445,521 | A | | 5/1984 | Grollier et al. |
|---|---|---|---|---|
| 5,266,303 | A | * | 11/1993 | Myers et al. |
| 6,056,946 | A | * | 5/2000 | Crudele et al. |
| 6,106,808 | A | * | 8/2000 | Bhatt et al. |
| 6,106,809 | A | * | 8/2000 | Bhatt et al. |
| 6,113,881 | A | * | 9/2000 | Bhatt et al. |
| 6,132,704 | A | * | 10/2000 | Bhatt et al. |
| 6,274,129 | B1 | * | 8/2001 | Bhatt et al. |
| 6,284,225 | B1 | * | 9/2001 | Bhatt et al. |

FOREIGN PATENT DOCUMENTS

EP 0619111 10/1994

* cited by examiner

*Primary Examiner*—Raj Bawa
(74) *Attorney, Agent, or Firm*—Matthew Boxer

(57) ABSTRACT

Hair spray compositions containing a carboxylated polyurethane resin, and having a low volatile organic content, are disclosed. The compositions have a low viscosity, and can be applied as a pump spray or as an aerosol, to hold the hair and impart excellent hair set retention properties. The hair spray compositions can be used with a curling iron or a blow dryer to style the hair.

5 Claims, No Drawings

METHOD OF STYLING HAIR WITH HAIR SPRAY COMPOSITIONS CONTAINING CARBOXYLATED POLYURETHANE RESINS

This is a divisional of Ser. No. 08/717,427, filed Sep. 20, 1996.

FIELD OF INVENTION

The present invention is directed to hair spray compositions that are applied to the hair to maintain the hair in a predetermined shape or configuration. The compositions impart excellent hair set retention, feel, and washability to sprayed hair. In particular, the present invention relates to aerosol and nonaerosol hair spray compositions comprising a carboxylated polyurethane resin, an organic solvent, and water, wherein the composition preferably is free of a neutralizing agent for the polyurethane resin.

BACKGROUND OF THE INVENTION

Normal hair can be so fine, limp, and lacking in body that the hair does not hold a hair set well. Furthermore, hair can lose body and be weakened as a result of being subjected to chemically active hair treatments, such as permanent waves and tints. Additionally, hair can be weakened even further by other contributing factors, such as bleaching by the sun or chlorinated swimming pool water.

Hair setting is basically the process of shaping wet hair by the steps of stretching the hair by curling the hair, fixing the hair in place by drying, then combing to give the finishing touches to provide the desired hairstyle. In particular, the setting of wet hair can be accomplished by making flat curls from strands of hair and fixing the curls with hairpins to product "pin curls." Similarly, the wet hair can be set by using any of a variety of rollers or curlers to mechanically fix the hair. In either case, winding of the wet hair is followed by drying, either ambient air drying, electric drying, or hot air, i.e., blow, drying.

The inherent problem encountered in hair setting is the natural tendency of hair to return to its natural shape. For example, set hair returns to its natural shape almost immediately if moistened. Likewise, high humidity conditions accelerate the tendency of hair to return to its natural shape. Therefore, intensive efforts have been directed toward providing a hair set with sufficient holding power to maintain a desired hairstyle until at least the next shampoo, and, therefore, giving the hair set a degree of permanency.

As indicated by the natural tendency of hair to return to its natural shape, hair is an elastic structure. As a result, slight deformations in hair structure resulting from setting the hair are completely reversible. However, the rate of return of hair to its natural shape is dependent upon the method used to deform, or set, the hair. Hair sets performed on wet strands of hair being rolled tightly, either in curls around the finger or on curlers, followed by drying the hair and unrolling the curlers after drying, corresponds to the release of the hair from a deformation-causing load. The deformation, or set, obtained can last for several days, but the set will not be retained if the hair is wetted.

Investigators have sought to delay the combined action of natural forces and moisture that cause hair to return to its original state by applying solutions containing naturally occurring or synthetic polymers after the hair is shaped into a desired configuration. When applied to shaped hair from aqueous or aqueous/alcoholic solutions, the polymers form a film on the hair, after drying, to help maintain the hair in the previously shaped configuration. The polymeric film promotes cohesion and gives stability to the hair set to maintain hold of the set. The principal objective of a setting lotion is to cover the previously styled hair with an invisible polymeric film that gives styled hair a degree of rigidity and protects the hairstyle against wind and humidity.

Hair spray products act in a similar manner. Hair spray products are applied to wet and/or dry hair and contain a polymer, or polymer mixture, that remains fixed on the previously styled hair and effects the hair in various ways. For example, a "mechanical" effect is exerted on each individual hair. The film-forming polymers are used to provide a flexible sheath of polymeric film on the shaped hair after drying, and, therefore, for mechanical reasons, retard the return of each individual hair to its natural shape. In addition, the polymeric film provides an overall stiffening of the hair. The hair behaves as if the individual hair strands are welded together, and the final hairstyle has better cohesion, therefore, resisting the natural forces that return the hair to its natural shape. Finally, the polymeric film protects the hair from humidity. The ability of the polymeric film to attract and absorb water preferably is minimal, such that the polymeric film retards moisture uptake by hair and retards the return of the hair to its natural state.

The general principles of hair setting are thoroughly discussed by C. Zviak, in *The Science of Hair Care,* Marcel Dekker, pp. 149–181 (1986). Zviak reviews both the polymers used in hair setting products and the formulation principles used to produce a hair set product that provides such beneficial hair set properties as improved hairstyle hold, easy application and combing, quick drying and nonstickiness, good hair body and bounce, increased hair volume and gloss, and hydrophobicity. It is evident that in the formulation of any end-use hairstyling product, some of these benefits must be sacrificed to some degree to achieve a competing benefit. Therefore, the formulation of hair set products has proved difficult.

As a result, to overcome some of the inherent disadvantages of the polymers utilized to set the hair, hair set products are made available in diversified forms in an attempt to minimize the drawbacks of the particular polymer used in the formulation. For example, hair set products are available as plasticizing lotions, plasticizing gels, aerosol foams, all-purpose lotions, hair sprays, holding lotions, conditioners, and shampoos.

Nonionic, cationic, and anionic polymers have been used in hair set products, with the anionic polymers providing the best hair set results. However, anionic polymers also have disadvantages, such as high water solubility, and, therefore, low hydrophobicity, and low substantivity on hair fibers, and, therefore, causing a crust and flaking due to easy elimination from the hair by combing and brushing. As a result, investigators have continued to search for compounds and compositions that provide the primary benefit of improved durability of the hair set.

Therefore, the use of resins, or polymers, in hair sprays is well known, as summarized in Grollier et al. U.S. Pat. No. 4,445,521. The resins typically used in hair sprays are linear vinyl (e.g., an alkyl vinyl ether) or acrylic (e.g., an alkyl acrylate) polymers prepared by copolymerizing two or more monomers in a free radical polymerization reaction. The vinyl and acrylic-based resins are used in relatively high concentrations in a hair spray composition to fix the hair in a particular configuration and to provide good hair set retention. However, at high concentrations, the vinyl and acrylic-based resins exhibit disadvantages that adversely affect the hair, such as poor combing and feel, and excessive stiffness, crust, and flaking.

The vinyl and acrylic-based hair fixative resins typically used in hair sprays were designed for use in anhydrous alcoholic hair spray compositions. The resins, therefore, have excellent compatibility with, and solubility in, alcohols (e.g., ethanol) used in pump spray compositions and hydrocarbons used as propellants in aerosol compositions. However, due to environmental and toxicological concerns, government regulations require a decrease in the amount of organic solvents used in hair spray and related compositions. Therefore, the alcohols and the hydrocarbon gases traditionally present in hair spray compositions are being replaced by water and water-soluble solvents, like dimethyl ether, that pose less harm to the environment.

The solvent changes required by government regulation made the traditional vinyl and acrylic-based resins unsuitable in hair spray compositions. For example, the presence of water in a hair spray composition increases the viscosity of the composition, thereby making spraying difficult to impossible when traditional resins are used. The relatively high viscosity of the compositions, therefore, requires a reduction in the resin concentration of the composition, which, in turn, results in insufficient hair set retention. The presence of water also increases the tackiness of the resin on the hair, thereby prolonging the drying time of the hair spray an the hair. Water also reduces the hair-wetting ability of the compositions, resulting in beading and flaking of the resin from the hair. In the case of aerosol products, the combination of water, resin, and propellant gas results in poor delivery and foaming of the composition, large aerosol particle size, and beading of the resin.

The need to change solvent systems for hair sprays again led investigators to search for new hair setting resins that overcome the disadvantages associated with the vinyl and acrylic resins. As set forth in European Patent Application 0 619 111, one class of resins is the polyurethanes. However, the hair fixative compositions disclosed in EP 0 619 111 require a base to neutralize, and solubilize, the polyurethane resin. It would be desirable to provide an aqueous hair spray composition containing a low amount of volatile organic compounds (VOC), that is free of a base, and that overcomes that disadvantages associated with traditional vinyl and acrylic resins.

SUMMARY OF THE INVENTION

The present invention is directed to aerosol and nonaerosol (i.e., pumpable) hair spray compositions containing hydrophilic, carboxylated polyurethane resins. The hair spray compositions impart good hair set retention and natural feel to sprayed hair, and provide superior retention of the hairstyle at high relative humidity. Such results are unexpected because traditional hair fixative resins are hydrophobic. In contrast, the carboxylated polyurethane resins are hydrophilic, yet provide a soft, natural feel to the hair, and the hair is not tacky.

The carboxylated polyurethane resins are soluble in a wide range of water-to-alcohol ratios, without the need to neutralize the resin with a base. Therefore, the hair spray compositions contain a low amount of VOC and are safe to the environment.

In particular, the present invention is directed to hair spray compositions comprising: (a) about 0.25% to about 6%, by total weight of the composition, of a carboxylated polyurethane resin, (b) 0% to about 80%, by total weight of the composition, of an alcohol, like ethanol, and (c) about 15% to about 80%, by total weight of the composition, of water. The hair spray compositions have a pH of about 6 to about 10.

The composition can be applied to the hair as a pump spray. Alternatively, if an aerosol composition is desired, the composition can further comprise about 5% to about 30%, by total weight of the composition, of a propellant. Optional ingredients also can be incorporated into the hair spray composition.

The polyurethane resins, also termed polycarbamyl polyglycols, have pendant carboxyl groups and are hydrophilic. The polyurethane resins have improved tear strength, excellent washability, good adhesion, and are soluble in water and polar solvents, thereby making them useful in hair spray compositions. In addition, the polyurethane resins form clear, low viscosity, solutions in neutral to slightly basic aqueous solvents. Solutions of the hydrophilic polyurethane resins, therefore, are sprayable.

In accordance with an important aspect of the present invention, hair spray compositions exhibit excellent sprayability when the viscosity of a 55% by weight VOC composition is about 1 to about 10 cps or about 1 to about 25 cps for an 80% by weight VOC composition. Compositions having such a viscosity provide a spray particle size of about 20 to about 150 microns.

In accordance with another important aspect of the present invention, the hair spray compositions exhibit improved washability from the hair when the carboxylated polyurethane resin has an acid value of at least 7 mg KOH/g (milligram potassium hydroxide per gram of resin), and preferably about 7 to about 50 mg KOH/g of resin. The polyurethane resins do not require neutralization with a base to provide a useful hair spray composition.

In accordance with one embodiment of the present invention, the carboxylated polyurethane resin used in the hair spray composition is produced by reacting: (a) a diol component comprising a polyoxyalkylene diol; (b) an alkylene glycol; (c) a diisocyanate; (d) water in an amount of about 0.001% to about 0.95% of the combined weight of the reactants; and (e) a 2,2-di(hydroxymethyl)alkanoic acid, preferably 2,2-di(hydroxymethyl)propionic acid, wherein the ratio of NCO (isocyanate) groups to OH (hydroxyl) groups in the water, diol, and glycol mixture, i.e., the R-value, is about 0.4 to about 1.1.

The hydrophilic carboxylated polyurethane resin contains polyoxyalkylene units, i.e., soft segments, and alkylene units, i.e., hard segments, connected through urethane linkages. Also incorporated into the polymer chain is a small amount of diol having a pendant carboxyl group. The polymer chain also contains urea linkages resulting from a reaction between the water and isocyanate groups, which modify the hair styling properties of the polyurethane.

The polyoxyethylene soft segments of the polyurethane resin impart hydrophilicity to the polyurethane. Soft segments derived from polyoxypropylene and polyoxytetramethylene diols provide a softer, but less hydrophilic, polyurethane. Hydrophilic polyurethane resins having improved strength and superior adhesive properties can be formed by using mixtures of polyoxyalkylene diols.

In another embodiment of the present invention, the carboxylated polyurethane resins used in the hair spray composition are produced from (a) a major portion of polyoxyethylene diol having a number molecular weight ($M_n$) of 6000 to 10,000; (b) an alkylene glycol, preferably diethylene glycol, cyclohexanedimethanol, or dipropylene glycol; (c) a diisocyanate; (d) water in the amount of about 0.01% to about 0.8% by weight; and (e) a 2,2-di-(hydroxymeth-yl)alkanoic acid, wherein the ratio of NCO to OH in the water, diol, and glycol mixture (i.e., the R-value)

is about 0.4 to about 0.98. These polyurethane resins are soluble in dilute (neutral to basic) aqueous solutions, and exhibit good sprayability, superior feel, low flaking, desirable crust, and good set retention when applied to hair. The polyurethane resins are hydrophilic, and provide a soft feel in a hydrated state. In a particular embodiment of a polyurethane resin produced with a major portion of polyoxyethylene diol, water is added in the amount of about 0.04% to about 0.25% by weight, and the ratio of NCO to OH of the water, diol and glycol mixture (i.e., the R-value) is about 0.55 to about 0.98 to provide a carboxylated polyurethane resin having improved adhesiveness to the hair and improved slip on the hair, i.e., good combing properties.

Another aspect of the present invention is to provide a hair spray composition that provides good hair set retention at high relative humidity and that imparts a natural feel to the hair. Accordingly, a hydrophilic polyurethane resin incorporated into a present hair spray composition has a weight average molecular weight ($M_w$) of about 15,000 to about 150,000, and Preferably about 15,000 to about 100,000. The polyurethane resins also have a polydispersibility index (PDI) of about 1 to about 4, and preferably about 1 to about 3. Preferred polyurethane resins have an R-value of about 0.5 to about 1.

In accordance with another important aspect of the present invention, hair spray compositions of the present invention incorporating a carboxylated polyurethane resin having an $M_w$ greater than 30,000 impart a set retention of 62% or higher at 70% and 85% relative humidity. Hair spray compositions incorporating a polyurethane resin having an $M_w$ below 64,000 provide a hair curl compression in the range between 133 to 296 gram force. In addition, hair spray compositions incorporating a carboxylated polyurethane resin having an $M_w$ below 64,000 further improves hair hand feel. A polyurethane resin having an $M_w$ less than 40,000 and R-value less than 0.75 provides sprayed hair having the best feel and the least amount of flaking.

DETAILED DESCRIPTION OF THE INVENTION

The present hair spray compositions are sprayable hair styling aids containing a carboxylated polyurethane resin. The polyurethane resins are soluble in water and in a broad range of water/alcohol mixtures, thereby permitting the preparation of aerosol and nonaerosol, i.e., pump spray, compositions containing a reduced amount of volatile organic compounds (VOC). The hair spray compositions also can contain propellant gases, and can be applied as an aerosol spray. The carboxylated polyurethane resins possess thermal properties that allow styling of the hair with curling irons or a blow dryer. The polyurethane resin-based hairstyle compositions, therefore, overcome problems and disadvantages associated with prior acrylic and vinyl-based hair fixative resins, and provide improved styling, hair set retention, hair feel, washability, and spray properties.

In particular, the present hair spray compositions comprise about 0.25% to about 6%, and preferably about 0.5% to about 6%, by total weight, of a carboxylated polyurethane resin. To achieve the full advantage of the present invention, the composition comprises about 1% to about 5%, by weight of the composition, of a carboxylated polyurethane resin.

The polyurethane resins are linear, hydroxyl-terminated copolymers having pendant carboxylic acid groups. In accordance with an important feature of the present invention, the polyurethane resins can be solubilized in water, or in a hydroalcoholic solution, in the absence of a base.

The carboxylated polyurethane resins are soft and flexible, and have a melting point of about 40° C. to about 120° C., and preferably about 60°0 C. to about 100° C. To achieve the full advantage of the present invention, the polyurethane resins have a melting point of about 70° C. to about 90° C.

The carboxylated polyurethane resins also are (a) sprayable, (b) soluble in hydroalcoholic solutions, (c) propellant tolerant, and (d) fast drying. The polyurethane resins also exhibit good wet combing properties, and are washable from the hair.

A polyurethane resin incorporated into a present hair spray composition comprises a reaction product of a diol component, an alkylene glycol, an aliphatic diisocyanate, water, and a 2,2-di-(hydroxy-methyl)alkanoic acid. An amine, such as diglycolamine, can be substituted for at least a portion of the water in the reaction mixture. Aqueous solutions of the hydrophilic carboxylated polyurethane resins have low viscosities, and impart a soft feel, good set retention, reduced flaking and crust, and improved hair conditioning properties to sprayed hair.

In one embodiment, the polyurethane resin comprises the reaction product of: a diol component comprising a polyoxyalkylene diol, preferably a polyoxyethylene diol having an $M_n$ of about 400 to about 20,000, a polyoxypropylene diol having an $M_n$ of about 200 to about 2500, a block copolymer of ethylene oxide and propylene oxide having an $M_n$ of about 1,000 to about 9,000, or a polyoxytetramethylene diol having an $M_n$ of about 200 to about 4,000; about 0.01% to about 10% by weight of a low molecular weight alkylene glycol selected from the group consisting of ethylene glycol, propylene glycol, 2-ethyl-1,3-hexanediol, tripropylene glycol, triethylene glycol, 2,4-pentane-diol, 2-methyl-1,3-propanediol, 2-methyl-1,3-pentane-diol, cyclohexanediol, cyclohexanedimethanol, dipropylene glycol, diethylene glycol, and mixtures thereof; an organic diisocyanate; a 2,2-di-(hydroxy-methyl)alkanoic acid; and water in an amount of about 0.001% to about 0.95% by weight of the reaction mixture, wherein the NCO/OH ratio (i.e., the R-value) is about 0.4 to about 1.1, and preferably about 0.4 to about 1. To achieve the full advantage of the present invention, the R-value is about 0.5 to about 0.98.

An amine can be used in the reaction mixture for at least a portion of the water. The amine can be added to the reaction mixture in an amount of about 0.01% to about 0.8% by weight amine, preferably about 0.02% to about 0.5% amine to about 0.01% to about 0.2% water in the reaction mixture. Amines that can be used in the reaction mixture are ethylenediamine, propylenediamine, monoethanolamine, diglycolamine, and JEFFAMINE D1-230, D-400, D-2000, D-4000, ED-0600, ED-900, or ED-2001. The hydroxylamines and the JEFFAMINE products are manufactured by Texaco Chemical Company. Preferably, the amine is a hydroxylamine, and most preferably the amine is monoethanolamine and/or diglycolamine.

The polyoxyethylene diols are available from Union Carbide Corporation under the trademark CARBOWAX, such as CARBOWAX® 8000 and CARBOWAX® 1450 wherein the number represents number average molecular weight. The polyoxypropylene diols (PPG) are available from various sources, such as the PPG series of ARCO NIAX® PPG 1025, PPG 425, PPG 725, PPG 1225 and PPG 2025 and as R2134 (2200) and R2135 (4400), wherein the number represents number average molecular weight. Triols are also available from ARCO as NIAX® Polyols 11-34, LG-650, LG-56, LG-168, LHT-28, LHT-240. The polyoxytetramethylene diols are available from E.I. DuPont de Nemours as TERATHANE 600, 1000, 1400, 2000, and 2900. Polyetherpolycarbonate is available from BASF under the tradename polytetrahydrofuran 1000 CD and 2000 CD.

A block polyoxyalkylene polymer also can be used in the reaction. For example, a propylene oxide terminated block of ethylene glycol manufactured by BASF under the tradename PLURONIC R and an ethylene oxide terminated block of propylene glycol manufactured by BASF under the tradename of PLURONIC can be used for the polyoxyalkylene in the reaction. Examples of the block copolymers of the sequential addition of ethylene oxide and propylene oxide to ethylene diamine are made by BASF under the tradename of PLURONIC, such as PLURONIC F68, F64, F127, L35, L92, L82, 17R2, and 25R2.

Preferably, the polyoxyalkylene diol used in forming the hydrophilic polyurethane resin is polyoxyethylene diol. The blends of polyoxyalkylene diols contain at least about 10% polyoxyethylene diol, preferably, at least about 20% polyoxyethylene diol, and most preferably, at least about 25% polyoxyethylene diol, by weight.

The amount of polyoxyalkylene diol having a molecular weight of 400 to 20,000 in the polyurethane resin can vary from about 10% to about 90%, preferably about 30% to about 90%, and most preferably about 40% to about 90%, by weight, and the number average molecular weight ($M_n$) of the polyoxyalkylene diol can vary from about 400 to about 20,000, preferably from about 800 to about 15,000, and more preferably from about 1000 to about 12,000.

The alkylene glycols can be purchased from numerous sources. For example, propylene glycol can be purchased from Aldrich Chemical Company as 1,2-propanediol. The amount of the alkylene glycol (hard segment) component in the polyurethane resin can be about 0.01% to about 20%, preferably about 0.05% to about 15%, more preferably about 0.1% to about 12%, still more preferably about 0.5% to about 10%, and most preferably about 1% to about 8%, by weight of the reaction mixture.

The diisocyanate in the reaction mixture can be an aliphatic diisocyanate, an aromatic diisocyanate, or a mixture thereof. The aliphatic diisocyanates are preferred. An especially preferred diisocyanate is methylene bis(cyclohexyl-4-isocyanate). Other examples of diisocyanates are trimethylhexamethylene diisocyanate and isophorone diisocyanate. Representative examples of the preferred aliphatic diisocyanates include, but are not limited to, tetramethylene diisocyanate, hexamethylene diisocyanate, trimethylene diisocyanate, cyclohexyl-1,2-diisocyanate, and cyclohexyl-1,4-diisocyanate. Examples of aromatic diisocyanates include 2,4-toluene diisocyanate and 2,6-toluene diisocyanate. Also suitable are the isocyanate equivalents which form urethane linkages, exemplified by nitrile carbonates, such as adiponitrile carbonates of U.S. Pat. No. 4,810,543, incorporated herein by reference. The amount of diisocyanate varies from about 3% to about 80%, preferably from about 4% to about 70%, more preferably from about 5% to about 60%, still more preferably from about 6% to about 55%, and most preferably from about 6.5% to about 50%, by weight. The polyurethane resins are prepared by reacting the polyoxyalkylene diols with the diisocyanates.

The amount of water in the reaction mixture is about 0.01% to about 0.75%, and more preferably about 0.35% to about 0.55%, by weight of the reaction mixture.

The amount of 2,2-di-(hydroxymethyl) alkanoic acid in the reaction mixture is about 0.1% to about 30%, preferably about 0.2% to about 20%, more preferably about 0.3% to about 10%, still more preferably about 0.4% to about 8%, and most preferably about 0.5% to about 7.0%, by weight. Preferably the 2,2-di-(hydroxymethyl)alkanoic acid is dimethylolpropionic acid. The final reaction product has an acid value of at least about 0.2, preferably at least about 0.5, and more preferably at least about 1.

The ratio of NCO to OH groups from the diol, alkylene glycol, amine and water (i.e., the R-value) in the reaction mixture is about 0.4 to about 1.1, preferably about 0.4 to about 1, and most preferably about 0.5 to about 0.98. The most preferred weight average molecular weight ($M_w$) of the carboxylated polyurethane resin is about 15,000 to about 150,000, preferably about 20,000 to about 70,000, and more preferably about 30,000 to about 65,000. The sum of all ingredients, including the diols, glycols, water, and diisocyanate in the reaction mixture totals 100% by weight.

In another embodiment, the hydrophilic polyurethane resin comprises a reaction product of: (a) a diol having a major portion of a polyoxyethylene diol having an $M_n$ of 6,000 to 10,000, and a minor portion of a polyoxypropylene diol having an $M_n$ of about 1,000 to about 3,500, a polyoxyethylene diol having an $M_n$ of about 600 to about 2000, or a mixture thereof; (b) an alkylene glycol; (c) a diisocyanate; (d) water in an amount of about 0.01% to about 0.8% by weight, by weight of the reaction mixture; and (e) a 2,2-di(hydroxymethyl)alkanoic acid, and an equivalent mole weight ratio of NCO to OH of the water, diol and glycol of about 0.5 to about 0.98. Preferably at least 45% of the polyoxyethylene glycol of $M_n$ about 8000, more preferably at least about 55%, still more preferably at least about 65%, and most preferably at least 75%, by weight, is used in the total reaction mixture. The amount of the lower molecular weight polyoxyethylene diol having an $M_n$ of about 600 to about 2,000 is about 1% to about 15%, and preferably from about 2% to about 10%, by weight of the reaction mixture. Preferably, the alkylene glycol is diethylene glycol, cyclohexanedimethanol, dipropylene glycol, or a mixture thereof.

The 2,2-di-(hydroxymethyl)alkanoic acid preferably is dimethylolpropionic acid. The amount of dimethylolpropionic acid is about 0.1% to about 30%, preferably about 0.2% to about 20%, more preferably about 0.3% to about 10%, still more preferably about 0.4% to about 8%, and most preferably about 0.5% to about 2.7%, by weight of the reaction mixture. The final product has an acid value of at least about 0.2, and preferably at least about 1, mg KOH/g resin. To achieve the full advantage of the invention, the carboxylated polyurethane resin has an acid value of at least 7 mg KOH/g resin.

Alternatively, an amine can be used in place of a portion of the water in the reaction mixture. An amount of about 0.15% to about 0.6% amine, based on diglycolamine, is used with about 0.06% to about 0.5% of water, more preferably about 0.1% to about 0.40% of water, and most preferably of about 0.15% to about 0.30% of water, by weight.

The carboxylated polyurethane resins of this embodiment are especially useful in hair spray compositions because the polyurethane resins are soluble in ethanol/water mixtures, and in dilute neutral to basic aqueous solutions, to form low viscosity solutions. Solutions of the polyurethane resins also exhibit improved sprayability, improved feel of sprayed hair, low flaking and crust, and improved set retention of the hair.

For hair spray compositions, the hydrophilicity of the polyurethane resin is an unexpected important property in combination with other desirable properties, such as washability. Conventional hair fixative resins are hydrophobic materials that impart a stiff feel to hair. The present polyurethane resins are hydrophilic, which gives the hair a soft, natural feel, yet are adhesive to the hair and impart excellent hair set retention. It also has been found that the hair styling properties of the polyurethane resin can be affected by small changes in the amount of water, the ratio of NCO/OH, and the amount of the di(hydroxymethyl)alkanoic acid in the reaction mixture.

For hair spray compositions, the preferred diol is a polyoxyethylene diol, preferably a polyoxyethylene diol of $M_n$ about 6000 to about 10,000, alternatively with about 1% to about 10% by weight of a polyoxyethylene diol of $M_n$ about 1000 to 2500. The preferred water level is about 0.01% to about 0.65%, preferably about 0.02% to about 0.60%, more preferably about 0.05% to about 0.55%, and most preferably about 0.10% to about 0.50%, by weight.

Further, it has unexpectedly been found that the weight average molecular weight of these polymers can be decreased or increased by up to about 20,000 by modifying the amount of water in the reaction mixture within a predetermined range. The above-described carboxylated polyurethane resins preferably have an $M_w$ of the reaction product of about 15,000 to about 100,000, and preferably about 20,000 to about 55,000; and a kinematic viscosity at 3 wt. % in 55/42 ethanol/water (by weight) of about 4 to about 40 centistokes (cs), formed from a range of water of about 0.1% to about 0.3% by weight of the reaction mixture, a NCO/OH ratio (i.e., R-value) of about 0.75 to about 0.95, and a range of dimethylolpropionic acid of about 0.5% to about 2.7% by weight of the reaction mixture.

A polyurethane resin having an $M_w$ of less than about 25,000 can be formed using a water level of about 0.25% to about 0.40% by weight of the reaction mixture, a ratio of NCO/OH about 0.60 to about 0.75, and a range of dimethylolpropionic acid of about 3.0% to about 6.5% by weight of the reaction mixture. The polyurethane resin has a kinematic viscosity at 3 wt. % in a 55/42 ethanol/water solution (by weight) of about 1 to about 10 cs. These polyurethane resins are useful as hair styling aids and forming low viscosity solutions in hair styling media. A polyurethane resin having an $M_w$ of about 55,000 to about 150,000 and a kinematic viscosity at 3 wt. % in 55/42 ethanol/water (by weight) of about 10 to about 60 cs can be formed using a range of water about 0.3% to about 0.45%, a preferred NCO/OH ratio of about 0.75 to about 0.98, and a range of dimethylolpropionic acid of about 0.5% to about 2.7%, by weight of the reaction mixture.

It also has been found that polyurethane resins prepared using an amount of water of about 0.08% to about 0.45% by weight in the reaction mixture, and a NCO/OH ratio of about 0.55 to about 0.95, preferably from about 0.6 to about 0.7, have a crust value of about 3 to about 5 and a set retention at 30 minutes and 75% relative humidity of about 80% to about 90%. An amount of water of about 0.15% to about 0.45% by weight in the reaction mixture and a NCO/OH ratio of about 0.6 to about 0.92, preferably from about 0.7 to about 0.9, can be used to provide polyurethane resins having a crust value of about 5 to about 9 and a set retention of about 85% to about 98% at 30 minutes and 75% relative humidity.

Alternatively, small amounts of diglycolamine can be substituted for water in the reaction mixture, e.g., about 0.02% to about 1%, preferably about 0.03% to about 0.75%, more preferably about 0.04% to about 0.5%, and most preferably 0.05% to about 0.4% diglycolamine, by weight, can be used in the reaction mixture.

The alkylene glycol used in this embodiment can be, for example, ethylene glycol, diethylene glycol, propylene glycol, dipropylene glycol, cyclohexanediol, 1,4-butanediol, cyclohexanedimethanol, tripropylene glycol, or triethylene glycol; preferably diethylene glycol, cyclohexanedimethanol, or dipropylene glycol; and most preferably diethylene glycol. The amount of the alkylene glycol (hard segments) in the reaction mixture is about 0.01% to about 20%, preferably about 0.05% to about 15%, more preferably about 0.1% to about 12%, still more preferably about 0.5% to about 10%, and most preferably about 1% to about 5%, by weight.

For hair spray compositions, the kinematic viscosity of a solution of the carboxylated polyurethane resin having a 55/42/3 weight ratio of ethanol/water/polyurethane resin is less than about 1,000 centistokes (e.g., about 1 to about 1,000 cs), preferably about 500 cs or less, more preferably about 100 cs or less, still more preferably less than about 80 cs, and most preferably less than about 60 cs.

In each embodiment, the polyurethane-forming reaction is catalyzed by known catalysts. Tin-containing catalysts, such as tin salts or organotin esters, for example, stannous octoate and dibutyltin dilaurate, or tertiary amines, such as triethylene diamine and N,N,N',N'-tetramethyl-1,3-butane diamine, are preferred. The catalyst is used in an amount effective to catalyze the reaction, i.e., about 0.001 to 1 weight percent of the total weight of the reaction mixture. Reaction temperature is about 40° C. to about 120° C.

In addition to the carboxylated polyurethane resin, the hair spray composition contains 0% to about 80%, by total weight of the composition, of an alcohol. Preferably, the composition contains 0% to about 55%, by weight, of an alcohol. In order to reduce the adverse environmental affects attributed to volatile organic compounds, the amount of alcohol is maintained at as low a level as possible without adversely affecting the esthetics or efficacy of the hair spray composition.

The alcohol typically used in the hair spray composition is ethanol, although isopropyl alcohol also can be incorporated into the composition. The carboxylated polyurethane resins are readily solubilized in a wide range of hydroalcoholic solutions, without the addition of basic neutralizer, thereby permitting a decrease in the amount of alcohol present in the hair spray composition.

The hair spray composition also contains 15% to about 95%, by total weight of the composition, of water. The amount of water is maximized in order to reduce the amount of VOC in the composition. Because the carboxylated polyurethane resins are hydrophilic, it is not necessary to include a base in the water to neutralize and solubilize the polyurethane resin.

Optional ingredients also can be incorporated into the hair spray composition. The identity of the optional ingredients is not limited as long as the optional ingredients do not adversely affect the esthetics or efficacy of the hair spray composition. For example, a hair spray composition containing only a polyurethane resin, water, and alcohol can be applied as a nonaerosol pump spray. The composition can be modified for application as an aerosol spray by incorporating about 5% to about 30%, by weight of the composition, of a propellant. The carboxylated polyurethane resin tolerates the propellant gases commonly used in aerosol compositions, such as the alkanes and carbon dioxide.

The optional propellant gas included in the hair spray compositions can be any liquefiable gas conventionally used for aerosol products. Examples of compounds that are suitable for use as propellants are trichlorofluoromethane, dichlorodifluoromethane, dichlorotetrafluoroethane, monochlorodifluoromethane, trichlorotrifluoroethane, dimethyl ether, propane, n-butane, and isobutane, either singly or admixed. Water-soluble gases such as dimethyl ether, carbon dioxide, and/or nitrous oxide also can be used to obtain aerosol sprays having reduced flammability.

Water-immiscible, liquified, hydrocarbon and halogenated hydrocarbon gases such as propane, butane, and chlorofluorocarbons can be used advantageously to deliver the contents of an aerosol container without the dramatic pressure drops associated with other immiscible gases. The head space left inside the aerosol container is not a factor because the liquified gas sits on top of the aqueous composition and the pressure inside the container is maintained at the vapor pressure of the saturated hydrocarbon vapor.

Other insoluble, compressed gases such as nitrogen, helium, and fully fluorinated oxetanes and oxepanes also are useful to deliver the compositions from aerosol containers. If the propellant, such as dimethyl ether, incorporates a vapor pressure suppressant (e.g., trichloroethane or dichloromethane), the amount of suppressant is included as part of the propellant for weight percentage calculations.

The hair spray compositions also can contain a variety of other nonessential, optional components. Such conventional optional ingredients are well known to those skilled in the art, e.g., emulsifiers, such as anionic or nonionic surfactants; preservatives, such as benzyl alcohol, methyl paraben, propyl paraben, or imidazolidinylurea; cationic conditioners, such as cetyl trimethyl ammonium chloride, stearyl dimethyl benzyl ammonium chloride, and di(partially hydrogenated tallow) dimethyl ammonium chloride; coloring agents, such as any of the FD&C or D&C dyes; perfume oils; and chelating agents, such as ethylene-diaminetetraacetic acid. These optional components generally are included individually at a level of 0% to about 5%, by weight of the total composition.

The aqueous formulations of the present invention also can contain conventional hair spray adjuvants in amounts which generally range from 0% to about 2%, by weight, and preferably 0% to about 1%, by weight. Among the additives which can be used are plasticizers such as glycols, phthalate esters, and glycerine, silicones, emollients, lubricants, and penetrants, such as various lanolin compounds, protein hydrolysates and other protein derivatives, ethylene adducts and polyoxyethylene cholesterol.

The hair spray compositions of the present invention are prepared by simply admixing and dissolving the carboxylated polyurethane resin and any optional ingredients into an aqueous or hydroalcoholic carrier. The resulting solution can be used in a pump spray, or can be pressurized by the addition of an aerosol propellant in accordance with methods well known in the art.

Polymer Preparation

Polyurethane Resin A

Polyoxyethylene diol having a number average molecular weight ($M_n$) of 8000 was heated under vacuum to 0.20% of water, and 744 parts of the dried diol was added to 20.8 parts of diethylene glycol, 18.6 parts of dimethylol propionic acid, and 5.51 parts of water. The mixture was heated with stirring until a homogeneous melt was obtained. Then, 135 parts of methylene bis-cyclohexyl-4-4'-diisocyanate were added during which the temperature decreased. The NCO/OH ratio (i.e., the R-value) was 0.50. When the temperature reached about 60° C., 2.25 ml of dibutyltin dilaurate was added, and the mass was allowed to exotherm to about 65° C. The mass was placed in an oven and held at 100° C. for 1.5 hours to complete formation of the polyurethane resin. At a concentration of 5 wt. %, the polyurethane resin dissolved in a 55/45 ethanol/water (wt/wt) solution to give a milky solution having a viscosity of 11 centipoise (cps). Upon addition of dilute ammonia, the viscosity did not change and the solution became clear.

Polyurethane Resin B

Polyoxyethylene diol having an $M_n$ of 8000 was heated under vacuum to 0.053% of water, and 473 parts of the dried diol was added to 13.2 parts of diethylene glycol, 11.5 parts of dimethylolpropionic acid, and 0.12 part of water. The mixture was heated with stirring until a homogeneous melt was obtained. Then, 69.7 parts of methylene bis-cyclohexyl-4-4'-diisocyanate were added during which the temperature decreased. The NCO/OH ratio was 0.90. When the temperature reached about 64° C., 0.75 ml of dibutyltin dilaurate was added. The mass was held at 100° C. for about one hour.

At 5 wt. % concentration, the polyurethane resin dissolved in 55/45 ethanol/water (wt/wt) solution to give a milky solution having a viscosity of 12 cps. At 5% concentration in 30/65 ethanol/water (wt/wt), the viscosity was 34 cps. Upon addition of dilute ammonia, the viscosity of the former solution was 13 cps, and the viscosity of the latter solution was 16 cps.

Polyurethane Resin C

Polyoxyethylene diol having an $M_n$ of 8000 was heated under vacuum to 0.030% of water, and 744 parts of the dried diol was added to 20.8 parts of diethylene glycol, 18.6 parts of dimethylolpropionic acid, and 0.078 part of water. The mixture was heated with stirring until a homogeneous melt was obtained. Then, 60 parts of methylene bis-cyclohexyl-4-4'-diisocyanate were added. The NCO/OH ratio was 0.50. When the temperature reached about 75° C., 2.25 ml of dibutyltin dilaurate was added, and the mass was allowed to exotherm. The mass was heated at 100° C. for 1.5 hours. The polyurethane resin was dissolved in water at 2 wt. % concentration to produce a solution with 4 cps viscosity.

At 5 wt. % concentration, the polyurethane resin dissolved in 55/45 ethanol/water (wt/wt) to give a slightly hazy solution having a viscosity of 9 cps. Upon addition of dilute ammonia, the solution had a viscosity of 7.5 cps, and became clear.

Polyurethane Resin D

Polyoxyethylene diol having an $M_n$ of 8000 was heated under vacuum to 0.0385% of water, and 744 parts of the dried diol was added to 20.8 parts of diethylene glycol, 18.6 parts of dimethylolpropionic acid, and 0.01 part of water. The mixture was heated with stirring until a homogeneous melt was obtained. Then, 100 parts of methylene bis-cyclohexyl-4-4'-diisocyanate were added. The NCO/OH ratio was 0.85. When the temperature reached about 68° C., 2.25 ml of dibutyl tin dilaurate was added and the mass exothermed. The mass was heated at 100° C. for 1.5 hours to complete formation of the polymer.

At 2 wt. % concentration of the polyurethane resin in water, the slightly hazy solution had a viscosity of 9 cps, and at 2.5 wt. % it had viscosity of 11.2 cps. At 5 wt. % concentration, the polyurethane resin dissolved in 55/45 ethanol/water (wt/wt) to give a hazy solution having a viscosity of 11 cps. At 5 wt. % concentration in 30/65 ethanol/water (wt/wt) the slightly hazy solution had a viscosity was 19 cps. Upon addition of dilute ammonia to bring the pH to 9.0, the viscosity of the former solution was 11.5 cps and that of the latter was 12.5 cps. Both solutions were clear.

Polyurethane Resin E

Polyoxyethylene diol having an $M_n$ of 8000 was heated under vacuum to 0.048% of water, and 744 parts of the dried diol was added to 21 parts of diethylene glycol, 38 parts of dimethylolpropionic acid, and 0.071 part of water. The mixture was heated with stirring until a homogeneous melt was obtained. Then, 132 parts of methylene bis-cyclohexyl-4-4'-diisocyanate were added. The NCO/OH ratio was 0.85. When the temperature reached about 73° C., 2.25 ml of dibutyltin dilaurate was added. The mass was heated at 100° C. for 1.5 hours to complete formation of the polymer.

The polyurethane resin was dissolved at 2 wt. % concentration in water, and the resulting solution had a viscosity of 9.5. At 2.5 wt. % concentration, the viscosity of the solution was 13.5 cps. Both solutions had a slight haze. At 5 wt. % concentration, the polyurethane dissolved in 55/45 ethanol/water (wt/wt) to give a viscosity of 10 cps. At 5 wt. % in 30/65 ethanol/water (wt/wt), the viscosity was 20 cps. Both solutions were hazy. Dilute ammonia was added to increase the pH to 9. The viscosity of the former solution was 10, and the viscosity of the latter solution was 13 cps. Both solutions were clear.

Polyurethan Resin F

Polyoxyethylene diol having an $M_n$ of 8000 was heated under vacuum to 0.050% of water, and 474 parts of the dried diol was added to 13 parts of diethylene glycol, 12 parts of dimethylolpropionic acid, and 0.15 part of water. The mixture was heated with stirring until a homogeneous melt was obtained. Then 73 parts of methylene bis-cyclohexyl-4-4'-diisocyanate were added. The NCO/OH ratio was 0.94. When the temperature reached about 61° C., 1.5 ml of dibutyltin dilaurate was added. The mass was heated at 100° C. for about one hour.

The polyurethane resin was dissolved at 5 wt. % concentration in 55/45 and 30/65 ethanol/water (wt/wt), giving viscosities of 12.0 and 23.5 cps, respectively. When the pH was raised with dilute ammonia, the viscosities were 9 and 14.4 cps, respectively.

Polyurethane Resin G

Polyoxyethylene diol having an $M_n$ of 8000 was heated under vacuum to 0.088% of water, and 744 parts of the dried diol was added to 21 parts of diethylene glycol, 4.3 parts of dimethylolpropionic acid, and 0.020 part of water. The mixture was heated with stirring until a homogeneous melt was obtained. Then, 81 parts of methylene bis-cyclohexyl-4-4'-diisocyanate were added. The NCO/OH ratio was 0.85. When the temperature reached about 61° C., 2.25 ml of dibutyltin dilaurate was added, and the mass was allowed to exotherm. The mass was heated at 100° C. for about one hour to complete formation of the polymer. At a 5 wt. % concentration, the polyurethane resin dissolved in 55/45 ethanol/water (wt/wt) to give a solution with a viscosity of 127 cps, and 2 cc of dilute ammonia in 180 grams reduced the viscosity to 69 cps. Both solutions had very small amounts of insolubles.

Polyurethane Resin H

Polyoxyethylene diol having an $M_n$ of 8000 was heated under vacuum to 0.037% of water, and 744 parts of the dried diol was added to 21 parts of diethylene glycol, 19 parts of dimethylolpropionic acid, and 0.023 part of water. The mixture was heated with stirring until a homogeneous melt was obtained. Then, 115 parts of methylene bis-cyclohexyl-4-4'-diisocyanate were added. The NCO/OH ratio was 0.98. When the temperature reached about 65° C., 2.25 ml of dibutyltin dilaurate was added, and the mass was allowed to exotherm. The mass was heated at 100° C. for about one hour to complete the polymerization.

At 5 wt. % concentration, the polyurethane resin dissolved in 55/45 ethanol/water (wt/wt) to give a clear solution with 5 pH and a viscosity of 1680 cps. Adding 2 cc dilute ammonia to 180 grams of solution reduced the viscosity of 225 cps. Both solutions were clear. Sodium bicarbonate also clarified the solution.

Polyurethane Resin I

Polyoxyethylene diol having an $M_n$ of 8000 was heated under vacuum to 0.208% of water, and 744 parts of the dried diol was added to 21 parts of diethylene glycol, 19 parts of dimethylolpropionic acid, and 2.90 part of water. The mixture was heated until a homogeneous melt was obtained. Then, 106 parts of methylene bis-cyclohexyl-4-4'-diisocyanate were added. The NCO/OH ratio was 0.50. When the temperature was about 63° C., 2.25 ml of dibutyltin dilaurate was added. The mass was allowed to exotherm, and then heated at 100° C. for 1.5 hours. At a concentration of 5 wt. % in 55/45 ethanol/water (wt/wt), the polyurethane resin produced a milky solution having a viscosity of 12.5 cps, and at 5 wt. % in 30/60 ethanol/water (wt/wt), the milky solution had a viscosity of 15.0 cps. Both solutions became clear upon the addition of dilute ammonia, with viscosities of 14 and 13 cps, and solutions of 2 wt. % and 2.5 wt. % polyurethane in water had viscosities of 4.5 and 7.0 cps, respectively.

Polyurethane Resin J

Polyoxyethylene diol having an $M_n$ of 8000 and polyoxyethylene diol having an average molecular weight of 1450 were heated under vacuum to 0.107% of water, and 1105 parts of the dried diol was added to 83 parts of ethylene glycol, 193 parts of dimethylolpropionic acid, and 1.485 part of water. The mixture was heated with stirring until a homogeneous melt was obtained. Then, 888 parts of methylene bis-cyclohexyl-4-4'-diisocyanate were added. The NCO/OH ratio was 0.93. When the temperature reached about 59° C., 3.0 ml of stannous octoate was added, and the mass was allowed to exotherm. The mass was heated at 100° C. for about one hour to complete formation of the polymer. The solutions had viscosities of 4.5 and 7.0 cps. About 5 wt. % polyurethane resin in 55/45 ethanol/water (wt/wt) gave a partial solution of polymer; particles were noted floating in the solvent. The solution had a viscosity of 12.5 cps. Upon addition of dilute ammonia, the viscosity was 14 cps and the solution was clear.

Polyurethane Resin K

Polyoxyethylene diol having an $M_n$ of 8000 was heated under vacuum to 0.271% of water, and 736 parts of the dried diol was added to 21 parts of diethylene glycol, 38 parts of dimethylolpropionic acid, and 0.271 part of water. The mixture was heated with stirring until a homogeneous melt was obtained. Then, 145 parts of methylene bis-cyclohexyl-4-4'-diisocyanate were added. The NCO/OH ratio was 0.75. When the temperature reached about 59° C., 1.85 ml of dibutyltin dilaurate was added, and the mass was allowed to exotherm. The mass was heated at 100° C. for about one hour to complete formation of the polymer. At a concentration of 5 wt. %, the polyurethane resin formed a milky solution in 55/45 ethanol/water (wt/wt) having a viscosity of 9.0 cps. The mixture was made basic with dilute ammonia to provide a water clear solution having a viscosity of 15.3 cps. The polyurethane resin was used as a hair styling aid.

Polyurethane Resin L

Polyoxyethylene diol having an $M_n$ of 8000 was heated under vacuum to 0.276% of water, and 736 parts of the dried diol was added to 21 parts of diethylene glycol, 24 parts of dimethylolpropionic acid, and 0.270 part of water. The mixture was heated with stirring until a homogeneous melt was obtained. Then, 124 parts of methylene bis-cyclohexyl-4-4'-diisocyanate were added. The NCO/OH ratio was 0.75. When the temperature reached about 56° C., 1.85 ml of dibutyltin dilaurate was added, and the mass was allowed to exotherm. The mass was heated at 100° C. for about one hour to complete formation of the polymer. The polyurethane resin formed a milky solution in 55/45 ethanol/water (wt/wt) at a concentration of 5 wt.%. The pH was 5.0 and the viscosity was 9.0 cps. The pH of about 20 cc of solution was increased to about 7 with dilute ammonia, potassium hydroxide, sodium bicarbonate, and lithium acetate dihydrate. The slightly basic solutions were water clear, and the viscosity of solution with ammonia was 15 cps.

Polyurethane Resin M

Polyoxyethylene diol having an $M_n$ of 1450 was heated under vacuum to a water level of 0.244% and the 227 parts of the dried diol was added to 156 parts of polyoxyethylene diol having an $M_n$ of 1000, 94 parts of polyoxyethylene diol having an $M_n$ of 600, 62 parts of polyoxyethylene diol having an $M_n$ of 400, 120 parts of ethylene glycol, 381 parts of polyoxytetramethylene glycol having an $M_n$ of 2000, 104 parts of polyoxypropylene glycol having an o of 1025, 93 parts of dimethylolpropionic acid, and 4.51 parts of water. The mixture was heated with stirring until a homogeneous melt was obtained. Then, 1026 parts of methylene bis-cyclohexyl-4-4'-diisocyanate were added. The NCO/OH ratio was 0.98. When the temperature reached about 50° C., 3.4 ml of stannous octoate ($T_9$) was added, and the mass was allowed to exotherm. The mass was heated at 100° C. for about one hour to complete formation of the polymer. The polyurethane resin had a tear strength of 520 pounds per inch, and modulus at 100% elongation of 1470 pounds per square inch compared to values of 260 pounds/inch and 670 pounds per square inch for a similar polyurethane resin made without dimethylolpropionic acid. The polyurethane resin had a water content of 21% and a linear expansion of 8% after exposure to water and similar polyurethane resin without any dimethylolpropionic acid had corresponding values of 25% and 11%. The polyurethane resin was dissolved in 75/25 tetrahydrofuran/ethanol to give a viscosity of 15 cps. Upon the addition of 5 wt. % water, the viscosity increased to 6120 cps.

Polyurethane Resin N

Polyoxyethylene diol having an $M_n$ of 8000 was heated under vacuum to 0.156% of water and 756 parts of the dried diol was added to 21 parts of diethylene glycol, 39 parts of dimethylolpropionic acid, and 0.25 part of water. The mixture was heated with stirring until a homogeneous melt was obtained. Then, 136 parts of methylene bis-cyclohexyl-4-4'-diisocyanate were added. The NCO/OH ratio was 0.75. When the temperature reached about 66° C., 1.85 ml of dibutyltin dilaurate was added, and the mass was allowed to exotherm. The mass was heated at 100° C. for about one hour to complete formation of the polymer. The polyurethane resin dissolved in a slightly basic 55/45 ethanol/water solution (wt/wt) at a concentration of 5 wt. % to produce a clear solution with a viscosity of 11 cps. The polyurethane resin was used to make an excellent hair styling aid. The polyurethane resin imparted a crust rating of 6.9, a feel of 5.5, a set retention of 95% at 30 minutes, and a set retention of 90% at 60 minutes to treated hair.

Polyurethane Resin O

Polyoxyethylene diol having an. $M_n$ of 8000 was heated under vacuum to 0.032% of water and 736 parts of the dried diol was added to 21 parts of diethylene glycol, 18 parts of dimethylolpropionic acid, and 2.06 parts of water. The mixture was heated with stirring until a homogeneous melt was obtained. Then, 113 parts of methylene bis-cyclohexyl-4-4'-diisocyanate were added. The NCO/OH ratio was 0.75. When the temperature reached about 65° C., 1.85 ml of dibutyltin dilaurate was added, and the mass was allowed to exotherm. The mass was heated at 100° C. for about one hour to complete formation of the polymer. The polymer dissolved in a slightly basic 55/45 ethanol/water solution (wt/wt) at a concentration of 5 wt. % to produce a clear solution with a viscosity of 13 cps. The polyurethane resin had a kinematic viscosity of 6.5 cs in 55/42/3 ethanol/water/polymer by weight solution. The polyurethane resin was used to make an excellent hair styling aid. The polyurethane resin imparted a crust rating of 4.2, a feel of 4.8, a flaking rating of 4.2, a set retention of 86% at 30 minutes, and a set retention of 73% at 60 minutes to treated hair.

Polyurethane Resin P

Polyoxyethylene diol having an $M_n$ of 8000 was heated under vacuum to 0.060% of water and 736 parts of the dried diol was added to 21 parts of diethylene glycol, 18 parts of dimethylolpropionic acid, and 2.84 parts of water. The mixture was heated with stirring until a homogeneous melt was obtained. Then, 139 parts of methylene bis-cyclohexyl-4-4'-diisocyanate were added. The NCO/OH ratio was 0.85. When the temperature reached about 64° C., 1.85 ml of dibutyltin dilaurate was added, and the mass was allowed to exotherm. The mass was heated at 100° C. for about one hour to complete formation of the polymer. The polyurethane resin had an $M_w$ of 76,000 and dissolved in a slightly basic 55/45 ethanol/water solution (wt/wt) at a concentration of 5 wt. % to give a viscosity of 18 cps. The polyurethane resin had a kinematic viscosity of 14.7 cs in 55/42/3 ethanol/water/polymer solution by weight. The polyurethane resin was used to make an excellent hair styling aid. The polyurethane resin imparted a crust rating of 8.3, a feel of 9.6, a flaking rating of 8.4. a set retention of 94% at 30 minutes, and a set retention of 91% at 60 minutes to treated hair.

Polyurethane Resin Q

Polyoxyethylene diol having an $M_n$ of 8000 was heated under vacuum to 0.074% of water and 281 parts added to 7.9 parts of diethylene glycol, 55 parts of dimethylolpropionic acid, and 1.38 parts of water. The mixture was heated with stirring until a homogeneous melt was obtained. Then, 109 parts of methylene bis-cyclohexyl-4-4'-diisocyanate were added. The NCO/OH ratio was 0.65. When the temperature reached about 70° C., 0.68 ml of dibutyltin dilaurate was added, and the mass was allowed to exotherm. The mass was heated at 100° C. for about one hour to complete formation of the polymer. The polyurethane resin dissolved in a slightly basic 55/45 ethanol/water solution (wt/wt) at a concentration of 5 wt. % to produce a clear solution with a viscosity of 10 cps.

Polyurethane Resin R

Polyoxyethylene diol having an $M_n$ of 8000 was heated under vacuum to 0.099% of water and 306 parts of the dried diol was added to 34 parts of a block copolymer of ethylene oxide and propylene oxide made by BASF under the tradename of F127, 9.5 parts of diethylene glycol, 27 parts of dimethylolpropionic acid, and 1.30 parts of water. The mixture was heated with stirring until a homogeneous melt was obtained. Then, 77 parts of methylene bis-cyclohexyl-4-4'-diisocyanate were added. The NCO/OH ratio was 0.65. When the temperature reached about 67° C., 0.68 ml of dibutyltin dilaurate was added, and the mass was allowed to exotherm. The mass was heated at 100° C. for about one hour to complete formation of the polyurethane resin. The polyurethane resin can be dissolved in slightly basic 55/45 ethanol/water (wt/wt) at a concentration of 5 wt. % to produce a clear solution with a viscosity of less than 20 cps.

Polyurethane Resin S

Polyoxyethylene diol having an $M_n$ of 8000 was heated under vacuum to 0.072% of water, and 343 parts of the dried diol was added to 18 parts of polyoxypropylene glycol of 425 molecular weight, 10 parts of diethylene glycol, 18 parts of dimethylolpropionic acid, and 0.43 part of water. The mixture was heated with stirring until a homogeneous melt was obtained. Then, 79 parts of methylene bis-cyclohexyl-4-4'-diisocyanate were added. The NCO/OH ratio was 0.85. When the temperature reached about 58° C., 0.68 ml of dibutyltin dilaurate was added, and the mass was allowed to exotherm. The mass was heated at 100° C. for about one hour to complete formation of the polymer. The polyurethane resin dissolved in 55/45 ethanol/water (wt/wt) at a concentration of 5 wt. % to produce a clear solution with a viscosity of 12 cps.

Polyurethane Resin T

Polyoxyethylene diol having an $M_n$ of 8000 was heated under vacuum to 0.061% of water, and 736 parts of the dried diol was added to 21 parts of diethylene glycol, 59 parts of dimethylolpropionic acid, and 1.11 part of water. The mixture was heated with stirring until a homogeneous melt was obtained. Then, 185 parts of methylene bis-cyclohexyl-4-4'-diisocyanate were added. The NCO/OH ratio was 0.85. When the temperature reached about 63° C., 1.85 ml of dibutyltin dilaurate was added, and the mass was allowed to exotherm. The mass was heated at 100° C. for about one hour to complete formation of the polymer. The polyurethane resin had an $M_w$ of 21,000 and dissolved in slightly basic 55/45 ethanol/water solution (wt/wt) at a concentration of 5 wt. % was clear and had a viscosity of 10 cps. The polyurethane resin had a kinematic viscosity of 6.15 cs in 55/42/3 ethanol/water/polymer solution by weight. The polyurethane resin was used as a hair styling aid, and imparted a crust rating of 6.3, a feel of 8.1, a flaking rating of 8.3, a set retention of 81% at 30 minutes, and a set retention of 68% at 60 minutes to treated hair.

Polyurethane Resin U

Polyoxyethylene diol having an $M_n$ of 8000 was heated under vacuum to 0.215% of water, and 736 parts of the dried diol was added to 21 parts of diethylene glycol, 59 parts of dimethylolpropionic acid, and 1.81 parts of water. The mixture was heated with stirring until a homogeneous melt was obtained. Then, 168 parts of methylene bis-cyclohexyl-4-4'-diisocyanate were added. The NCO/OH ratio was 0.65. When the temperature reached about 70° C., 1.85 ml of dibutyltin dilaurate was added, and the mass was allowed to exotherm. The mass was heated at 100° C. for about one hour to complete formation of the polyurethane resin. The polyurethane resin had an $M_w$ of 15,000 and dissolved in slightly basic 55/45 ethanol/water (wt/wt) solution at a concentration of 5 wt. % was clear and had a viscosity of 10 cps. The polyurethane resin had a kinematic viscosity of 4.60 cps in 55/42/3 ethanol/water/polymer solution by weight. The polyurethane resin can be used in a hair styling aid to impart superior soft feel, excellent set retention, low crust, and low flaking properties to treated hair. The hair styling aid imparted a crust rating of 4.5, a feel of 4.5, a flaking rating of 1.8, and a set retention of 85% at 30 minutes to treated hair.

Polyurethane Resin V

Polyoxyethylene diol having an $M_n$ of 8000 was heated under vacuum to 0.060% of water, and 736 parts of the dried diol was added to 21 parts of diethylene glycol, 18 parts of dimethylolpropionic acid, and 0.96 part of water. The mixture was heated with stirring until a homogeneous melt was obtained. Then, 114 parts of methylene bis-cyclohexyl-4-4'-diisocyanate were added. The NCO/OH ratio was 0.85. When the temperature reached about 63° C., 1.85 ml of dibutyltin dilaurate was added, and the mass was allowed to exotherm. The mass was heated at 100° C. for about one hour to complete formation of the polyurethane resin. The polyurethane resin dissolved in slightly basic 55/45 ethanol/water solution (wt/wt) at a concentration of 5 wt. % was clear and had a viscosity of 14 cps. The polyurethane resin had an $M_w$ of 40,000 and can be used in a hair styling aid to impart a superior soft feel, excellent set retention, low crust, and low flaking properties to hair. The hair styling aid imparted a crust rating of 4.9, a feel of 6.7, a flaking rating of 7, a set retention of 97% at 30 minutes, and a set retention of 95% at 60 minutes to treated hair.

Polyurethane Resin W

Polyoxyethylene diol having an $M_n$ of 8000 was heated under vacuum to 0.060% of water, and 336 parts of the dried diol was added to 9.3 parts of diethylene glycol, 27 parts of dimethylolpropionic acid, 8.2 parts of diglycolamine and 0.002 part of water. The mixture was heated with stirring until a homogeneous melt was obtained. Then, 73 parts of methylene bis-cyclohexyl-4-4'-diisocyanate were added. The NCO/OH ratio was 0.65. When the temperature reached about 65° C., 0.92 ml of dibutyltin dilaurate was added, and the mass was allowed to exotherm. The mass was heated at 100° C. for about one hour to complete formation of the polymer. The polyurethane resin dissolved in slightly basic 55/45 ethanol/water solution (wt/wt) at a concentration of 5 wt. % was clear. The polyurethane resin had a kinematic viscosity of 5.93 cs in 55/42/3 ethanol/water/polymer solution by weight.

Polyurethane Resin X

Polyoxyethylene diol having an $M_n$ of 8000 and polyoxyethylene diol having an $M_n$ of 1450 were heated under vacuum to 0.132% of water, and 291 parts of the higher molecular weight dried diol and 15.3 parts of lower molecular weight dried diol were added to 9.5 parts of dipropylene glycol, 27 parts of dimethylolpropionic acid, 34 parts of polyoxypropylene glycol of 425 molecular weight, and 1.146 part of water. The mixture was heated with stirring until a homogeneous melt was obtained. Then, 89 parts of methylene bis-cyclohexyl-4-4'-diisocyanate were added. The NCO/OH ratio was 0.65. When the temperature reached about 67° C., 0.68 ml of dibutyltin dilaurate was added, and the mass was allowed to exotherm. The mass was heated at 100° C. for about one hour to complete formation of the polymer. The polyurethane resin dissolved in slightly basic 55/45 ethanol/water solution (wt/wt) at a concentration of 5 wt. % was clear, and had a viscosity of 8 cps. The polyurethane resin can be used in a hair spray composition to give treated hair a superior soft feel, excellent set retention, low crust, and low flaking properties.

Polyurethane Resin Y

A batch of 13,147 parts of polyoxyethylene diol having an $M_n$ of 8000 was added to a five-gallon electrically heated reactor and heated under vacuum to dry the glycol. The dried diol was added to 368 parts of diethylene glycol and 321 parts of dimethylolpropionic acid, and the mixture was heated to 105° C. in order to melt the ingredients. The mixture was allowed to cool to about 175° F. to about 185° F. and the water level was analyzed by Karl Fisher method as 0.0675%. Then, 19.41 grams of water was added to the mixture to bring the total water to 28.75 grams of water.

A separate reactor contained 2073 parts of methylene bis(cyclohexyl-4-isocyanate). To the diols was added 33.04 cc of dibutyltin dilaurate. Then the isocyanate was heated to about 110°–115° F., and both liquids were forced out under nitrogen pressure using a piston cylinder at about a ratio of 0.1492. Twelve shots of liquid were pumped into a polypropylene tub and heated for one hour at 100° C. The NCO/OH ratio as 0.85.

The polyurethane resin was dissolved at 3 wt. % solids in 55/45 ethanol/water solution (wt/wt) and gave viscosities of 11 cps using a Brookfield viscometer. The polyurethane resin had a kinematic viscosity of 7.67 cs in 55/42/3 ethanol/water/polymer solution by weight. The polymer had an $M_w$ of 40,000.

The polyurethane resin was used in a hair spray to give hair a superior soft feel, excellent set retention, low crust, and low flaking properties.

Polyurethane Resin Z

A batch of 13,147 parts of polyoxyethylene diol having an $M_n$ of 8000 was added to a five-gallon electrically heated reactor and heated under vacuum to dry the glycol. The dried diol was added to 368 parts of diethylene glycol and 321 parts of dimethylolpropionic acid, and the mixture was heated to 105° C. in order to melt the ingredients. The mixture was allowed to cool to about 175° F. to about 185° F. and a sample of the mixture was taken and analyzed for its water content by Karl Fisher method. The mixture had a water content of 0.0625% water and 26.66 grams of water was added to the mixture to bring the total water to 35.31 grams of water.

A separate reactor contained 2162 parts of methylene bis(cyclohexyl-4-isocyanate). To the diols was added 33.04 cc dibutyltin dilaurate. Then the diisocyanate was heated to about 110°–115° F., and both liquids were forced out under nitrogen pressure using a piston cylinder at about a ratio of 0.1555. Twelve shots of liquid were pumped into a polypropylene tub and heated for one hour at 100° C. The NCO/OH ratio was 0.85.

The polyurethane resin was dissolved at 3% solids in 55/45 ethanol/water solution (wt/wt) and gave a viscosity of 11.5 cps using a Brookfield viscometer. The polyurethane resin had a kinematic viscosity of 9.81 Cs in 55/42/3 ethanol/water/polymer solution by weight, and an $M_w$ of 49,000.

Polyurethane Resin AA

Polyoxyethylene diol having an $M_n$ of 8000 was heated under vacuum to 0.028% of water, and 736 parts of the dried diol was added to 21 parts of cyclohexanedimethanol, 18 parts of dimethylolpropionic acid, and 1.21 parts of water. The mixture was heated with stirring until a homogeneous melt was obtained. Then, 102 parts of methylene bis-cyclohexyl-4-4'-diisocyanate were added. The NCO/OH ratio was 0.85. When the temperature reached about 65° C., 1.85 ml of dibutyltin dilaurate was added, and the mass was allowed to exotherm. The mass was heated at 100° C. for about one hour to complete formation of the polyurethane resin. The polyurethane resin can be dissolved in slightly basic 55/45 ethanol/water solution (wt/wt) at a concentration of 5 wt. % to give a low viscosity clear solution. The polyurethane resin was used in a hair spray composition to give treated hair a superior soft feel, excellent set retention, low crust, and low flaking properties.

Polyurethane Resin BB

A polyoxyethylene diol having an $M_n$ of 8000 was heated under vacuum to 0.048% of water, then 744 parts of the dried diol was added to 21 parts diethylene glycol, 4.3 parts dimethylolpropionic acid, and 0.37 parts water. The resulting mixture was heated, with stirring, until a homogenous melt was obtained. Then, 88 parts methylene bis-cyclohexyl-4-4'-diisocyanate was added to the mixture. The NCO/OH ratio was about 0.98. When the temperature reached about 65° C., 2.25 ml of dibutyl tin dilaurate was added to the mixture, and the mass exothermed. The mass then was heated to 100° C., and held at 100° C. for about one hour to complete polyurethane formation. The polyurethane resin had an $M_w$ of 141,000. At 5% concentration, the polyurethane resin dissolved in 55/45 ethanol water to give a solution having a viscosity of 180 cps. At a concentration of 3%, in 60/40 propylene glycol/water, the solution had a viscosity of 5300 cps. A gel containing 19% of the polyurethane resin in 20/80 propylene glycol/water was tough, exceptionally clear, and adhered to glass. The viscosity of the gel was reduced by raising the pH about 7.0.

Polyurethane Resin CC

A polyoxyethylene diol having an $M_n$ of 8000 was heated under vacuum to 0.037% of water, then 744 parts of the dried diol was added to 21 parts diethylene glycol, 18.6 parts dimethylolpropionic acid, and 0.23 parts water. The resulting mixture was heated, with stirring, until a homogenous melt was obtained. Then, 115 parts methylene bis-cyclohexyl-4-4'-diisocyanate was added to the mixture. The NCO/OH ratio was about 0.98. When the temperature reached about 65° C., 2.25 ml dibutyl tin dilaurate was added to the mixture, and the mass exothermed. The mass then was heated to 100° C., and held at 100° C. for about one hour to complete polyurethane formation. The polyurethane resin had an $M_w$ of 63,000. At 5% concentration, the polyurethane resin dissolved in 55/45 ethanol water to give a solution having a viscosity of 1680 cps, and a reduced viscosity of 225 cps upon the addition of 2 ml ammonia to 180 grams of the solution. At a concentration of 3%, in 60/40 propylene glycol/water, the solution had a viscosity of 144 cps. A gel containing 19% of polymer in 20/80 propylene glycol/water was tough, exceptionally clear, and adhered to glass, displaying improved adhesive properties compared to gels made using a polyurethane without the alkanoic acid.

Polyurethane Resin DD

A polyoxyethylene diol having an $M_n$ of 8000 was heated under vacuum to 0.062% of water, then 470 parts of the dried diol was added to 13.2 parts diethylene glycol, 11.4 parts dimethylol propionic acid, and 0.55 parts water. The resulting mixture was heated, with stirring, until a homogenous melt was obtained. Then, 76 parts methylene bis-cyclohexyl-4-4'-diisocyanate was added to the mixture. The NCO/OH ratio was about 0.90. When the temperature reached about 61° C., 1.44 ml dibutyl tin dilaurate was added to the mixture, and the mass exothermed. The mass was heated to 100° C., and held at 100° C., for about one hour to complete formation of the polyurethane. The polyurethane resin had an $M_w$ of 46,000. At a 5% concentration, the polyurethane dissolved in 55/45 ethanol water to give a solution having a viscosity of 13 cps, and a reduced viscosity of 12 cps upon the addition of 2 ml ammonia to 180 grams of the solution. At a concentration of 3%, in 60/40 propylene glycol/water, the solution had a viscosity of 64 cps. At a concentration of 5%, in 30/70 ethanol/water, the solution had a viscosity of 34 cps, and upon neutralization, the viscosity dropped to 16 cps. A gel made with 19% of polyurethane in 20/80 propylene glycol/water was tough, exceptionally clear, and adhered to glass, displaying improved adhesive properties compared to gels made using polymer without the alkanoic acid.

An important property of a hair spray composition is the ability to wash the hair setting resin from the hair, and thereby avoid polymer build-up on the hair. In accordance with an important feature of the present invention, the carboxylated polyurethane resin used in the hair spray composition can be removed from the hair by simply shampooing the hair. The unexpected washability of the hair spray composition is attributed to the hydrophilic nature of the polyurethane resin, and especially to the acid value of the carboxylated polyurethane resin. When the acid value of the carboxylated polyurethane resin is at least about 7 mg KOH/g of resin, e.g., about 7 to about 50 mg KOH/g of resin, the polyurethane resin can be rinsed from the hair during shampooing without the need to neutralize the resin with an organic base.

The acid value is an indication of the number pendant carboxylic acid groups on the polyurethane resin backbone. Although noncarboxylated polyurethane resins are hydrophilic, they are difficult to wash from the hair in a short time. Washability is enhanced by incorporating pendant carboxylic acid groups onto the polyurethane backbone.

The effect of acid value is illustrated in Tables 1 and 2, wherein it is shown that washability is independent of $M_w$ or R-value, but varies with acid value. In effect, carboxylated polyurethane resins having an acid value of at least about 7 mg KOH/g of resin or greater, i.e., about 7 to about 50 mg KOH/g resin, had improved washability over resins having an acid value less than 7 mg KOH/g resin.

TABLE I

PROPERTIES OF POLYURETHANE RESINS
(R-VALUE = 0.73 TO 0.98)

| Polyurethane Resin | R-value | Water | Acid Value[1] | Molecular Weight[2] | PDI[3] | Washability[4] |
|---|---|---|---|---|---|---|
| 1 | 0.98 | low | 0.42 | 174,000 | 2.00 | no |
| 2[16] | 00.98 | low | 2.28 | 141,000 | 2.0 | yes |
| 3 | 0.84 | low | 8.01 | 28,000 | 2.0 | no |
| 4 | 0.93 | low | 7.88 | 37,000 | 2.00 | yes |
| 5 | 0.98 | low | 8.28 | 63,000 | 2.00 | yes |
| 6 | 0.98 | medium | 0.50 | 188,000 | 2.20 | no |
| 7 | 0.85 | medium | 2.47 | 64,000 | 1.90 | no |
| 8 | 0.85 | medium | 8.62 | 37,000 | 1.70 | yes |
| 9 | 0.88 | medium | 7.87 | 30,000 | 1.60 | yes |
| 10 | 0.90 | medium | 7.70 | 43,000 | 1.80 | yes |
| 11 | 0.90 | medium | 8.04 | 39,000 | 1.70 | yes |
| 12 | 0.94 | medium | 7.78 | 39,000 | 1.80 | yes |
| 13 | 0.85 | high | 7.91 | 38,000 | 1.80 | yes |
| 14 | 0.90 | high | 7.70 | 46,000 | 1.90 | yes |
| 15 | 0.73 | low | 15.19 | 23,000 | na | yes |
| 16 | 0.73 | low | 7.10 | 59,000 | na | yes |
| 17 | 0.98 | low | 3.66 | 117,000 | na | no |
| 18 | 0.98 | low | 4.03 | 85,000 | na | no |

[1]The acid value was measured by titrating a solution of the resin with potassium hydroxide, the acid vatue is expressed in milligrams of KOH per gram of polyurethane resin;
[2]The molecular weight is the weight average molecular weight ($M_W$) measured by size exclusion chromatography using polyethylene glycol calibration standards;
[3]PDI is an abbreviation for "polydispersity index," i.e., the ratio [Weight average molecular weight]/[Number average molecular weight], which measures the relative spread in the molecular weight of the polyurethane resin; and
[4]The washability of the resin was determined by applying 3 wt. % solution of polyurethane resin onto clean, 2 gram, 6-inch long hair tresses, allowing the hair to dry, then washing the hair tresses with shampoo and warm water for about 3 minutes.

TABLE 2

PROPERTIES OF POLYLRETHANE RESINS
(R-VALUE = 0.65 TO 0.85)

| Polyurethane Resin | R-value | Water | Acid Value[1] | Molecular Weight[2] | Washability[4] |
|---|---|---|---|---|---|
| 19 | 0.75 | med | 16.30 | 18,000 | yes |
| 20[5] | 0.65 | high | 8.22 | 26,000 | ves |
| 21 | 0.65 | med | 17.02 | 16,000 | yes |
| 22[6] | 0.85 | low | 23.31 | 21,000 | yes |
| 23[7] | 0.75 | high | 22.48 | 24,000 | yes |
| 24[8] | 0.85 | high | 7.75 | 76,000 | yes |
| 25 | 0.75 | high | 16.53 | 20,000 | yes |
| 26[9] | 0.65 | high | 24.22 | 15,000 | yes |
| 27 | 0.85 | med | 16.37 | 27,000 | yes |
| 28 | 0.75 | low | 16.45 | 25,000 | yes |
| 29[10] | 0.75 | med | 8.11 | 35,000 | yes |
| 30[11] | 0.85 | low | 8.01 | 40,000 | yes |

[5]Polyurethane Resin W;
[6]Polyurethane Resin T;
[7]Polyurethane Resin N;
[8]Polyurethane Resin P;
[9]Polyurethine Resin U;
[10]Polyurethane Resin O; and
[11]Polyurethane Resin V.

A hair spray composition of the present invention also can be evenly delivered as a spray. In particular, the carboxylated polyurethane resins are suitable for preparing hair spray compositions containing various levels of volatile organic compounds (VOC). Hair spray compositions containing 55% VOC and having good spray properties have a viscosity of about 1 to about 10 cps. Hair spray compositions containing 80% VOC and having good spray properties have a viscosity of about 1 to about 25 cps. Accordingly, it was found that to provide a hair spray composition having excellent spray characteristics, the $M_w$ of the carboxylated polyurethane resin is about 15,000 to about 70,000, and preferably about 20,000 to about 65,000.

Aerosol and nonaerosol hair spray compositions of the present invention were prepared by dissolving 5%, by weight, of a carboxylated polyurethane resin in a blend of water and ethanol, then pouring the resulting solution into an aerosol can. The filled can was crimped with a conventional aerosol valve. Then 30 weight % dimethyl ether (i.e., DME), was charged into the aerosol can. The nonaerosol, pump hair spray compositions were prepared by simply dissolving the polyurethane resin in a water/ethanol blend. The composition of the examples set forth in Tables 3 and 4 are summarized below:

| Aerosol Hair Spray (55% VOC) | |
|---|---|
| Polyurethane resin | 5 (% wt.) |
| Ethanol | 25 |
| DME | 30 |
| Water | 40 |

| Aerosol Hair spray (80% VOC) | |
|---|---|
| Polyurethane resin | 5 (% wt.) |
| Ethanol | 50 |
| DME | 30 |
| Water | 15 |

| Pump Hair Spray (80% VOC) | |
|---|---|
| Polyurethane resin | (% wt.) |
| Ethanol | 80 |
| water | 15 |

| Pump Hair Spray (55% VOC) | | |
|---|---|---|
| | a | b |
| Polyurethane resin | 5 (% wt.) | 3 (% wt.) |
| Ethanol | 55 | 55 |
| Water | 40 | 42 |

The results summarized in Tables 3 and 4 show that the present hair spray compositions containing a carboxylated polyurethane resin can be applied to the hair as an aerosol spray or a pump spray. The results also illustrate that sprayability of the hair spray composition is optimized when the polyurethane resin has an $M_w$ of about 15,000 to about 70,000.

TABLE 3

SPRAYING PROPERTIES OF HAIR SPRAY COMPOSITIONS CONTAINING 5% WT/WT OF A POLYURETHANE RESIN

| Polyurethane Resin | Viscosity [mm²/S][12] | | Aerosol Spray Pattern[13] | | Pump Spray Pattern[14] | |
|---|---|---|---|---|---|---|
| | 55% VOC | 80% VOC | 55% VOC | 80% VOC | 55% VOC | 80% VOC |
| 1 | 860.00 | v. viscous | v. bad | v. bad | bad | bad |
| 2[16] | 180.00 | v. viscous | v. bad | v. bad | bad | bad |
| 3 | 8.50 | 7.15 | good | good | good | good |
| 4 | 9.80 | 9.3 | marginal | good | good | good |
| 5 | 24.56 | 16.03 | bad | bad | marginal | marginal |
| 6 | 930.00 | v. viscous | v. bad | v. bad | bad | bad |
| 7 | 21.35 | 13.32 | v. bad | bad | marginal | marginal |
| 8 | 13.40 | 9.51 | marginal | good | good | good |
| 9 | 10.30 | 7.83 | marginal | good | good | good |
| 10 | 14.68 | 11.05 | bad | good | good | good |
| 11 | 13.20 | 9.41 | bad | good | good | good |
| 12 | 12.55 | 9.33 | bad | good | good | good |
| 13 | 12.79 | 10.03 | bad | good | good | good |
| 14 | 17.06 | 7.9 | bad | good | good | good |
| 15 | 8.33 | na[15] | good | na | good | na |
| 16 | 20.37 | na | marginal | na | marginal | na |
| 17 | 91.51 | na | bad | na | bad | na |
| 18 | 27.77 | na | bad | na | marginal | na |

[12]Previously centistokes (cs), 1 cs = 1 mm²/s, measured at 30° C. using a Ubbelohde capillary viscometer according to ASTM D 445; D 446, and ISO 3105;
[13]The spray pattern of the aerosol formulations was evaluated visually. A standard spray can with an actuator button having orifice diameter of 0.018 inch was used. The hair spray composition was sprayed in the air for about 10 seconds. A very bad or a bad spray pattern occurs when the composition sputters when leaving the actuator, the spray particles are too large or coarse (i.e., particle average diameter greater than 200 microns), the composition foams or clogs the actuator, or the spray cross section is narrow (i.e., less than 2 inches diameter). A marginal spray pattern is somewhat coarse, having an average particle diameter between 100 to 150 microns. A good spray pattern is when the spray leaves the can smoothly without sputtering or clogging, the spray particle size is fine, the particle average diameter is less than 100 microns, and there is no foaming;
[14]A standard pump bottle for hair spray compositions was used. The actuator orifice diameter was 0.018 inches. The hair spray composition was delivered from the bottle by manual pumping. The spray pattern was visually evaluated in the same as for aerosols, see footnote 6;
[15]na is not available; and
[16]Polyurethane Resin BB.

TABLE 4

HAIR SPRAY COMPOSITIONS (55% WT. ETHANOL)

| | 3% Polyurethane Resin | | 5% Polyurethane Resin | |
| --- | --- | --- | --- | --- |
| Polyurethane Resin | Viscosity [mm$^2$/s][12] | Pump Spray Pattern[14] | Viscosity [mm$^2$/s] | Pump Spray Pattern |
| 19 | 5.03 | good | 7.73 | good |
| 20[5] | 5.84 | good | 9.95 | good |
| 21 | 4.28 | good | 7.47 | good |
| 22[6] | 6.15 | good | 10.03 | marginal |
| 23[7] | 5.92 | good | 10.79 | marginal |
| 24[8] | 14.71 | marginal | 14.71 | marginal |
| 25 | 5.69 | good | 9.25 | good |
| 26[10] | 15.00 | good | 7.05 | good |
| 27 | 27.00 | good | 12.41 | marginal |
| 28 | 25.00 | good | 10.58 | marginal |
| 29[10] | 35.00 | good | 10.85 | marginal |
| 30[11] | 40.00 | marginal | 13.15 | marginal |
| Control[17] | 10.90 | good | 16.51 | bad |

[17]The control resin was octylacrylamide/acrylates/butylaminoethyl methacrylate copolymer, available as AMPHOMER, from National Starch and Chemical Corp., Bridgewater, NJ.

The hair spray compositions also impart good hold and hair set retention to treated hair. For example, a hair spray composition containing a carboxylated polyurethane resin having an $M_w$ of about 30,000 or greater provided equal or better set retention at 70% relative humidity than a control hair spray product containing the resin AMPHOMER. At 85% relative humidity, a hair spray composition containing a polyurethane resin having an $M_w$ of about 20,000 or greater provided equal or better set retention than a control hair spray product containing AMPHOMER. AMPHOMER is an acrylic copolymer resin and is widely used resin in commercial hair spray products. Hair spray products containing AMPHOMER, therefore, are used as a control for comparison to hair spray compositions containing a carboxylated polyurethane resin.

In tests designed to test the ability of a present hair spray composition to hold the hair, hair spray compositions containing 3 parts by weight carboxylated polyurethane resin dissolved in a mixture of 55 parts by weight ethanol and 42 parts by weight water were prepared. Because sprayability of the composition is optimized when the $M_w$ of the polyurethane resin is about 70,000 or less, polyurethane resins having an $M_w$ of about 65,000 or greater were not used in these tests. The polyurethane resins and the test results are summarized in Table 5. Each polyurethane resin used in these tests had an acid value of at least 7 mg KOH/g resin, and typically about 7.5 to about 50 mg KOH/g resin.

TABLE 5

| Example | Polyurethane Resin | R-Value [NCO/OH] | Molecular Weight ($M_W$) | % Static Set Retention 1 hr. @ 70% R.H. (95% C.L.)[18] | Crust [gram-force] | Washability |
| --- | --- | --- | --- | --- | --- | --- |
| 1 | 3 | 0.84 | 28,000 | 71.00(=) | 133 (+) | yes |
| 2 | 4 | 0.93 | 37,000 | 82.50(+) | 244 (+) | yes |
| 3 | 5 | 0.98 | 63,000 | 86.71(+) | 267 (+) | yes |
| 4 | 8 | 0.85 | 37,000 | 81.00(=) | 188 (+) | yes |
| 5 | 9 | 0.88 | 30,000 | 66.50(+) | 155 (+) | yes |
| 6 | 10 | 0.90 | 43,000 | 83.24(+) | 297 (=) | yes |
| 7 | 11 | 0.90 | 39,000 | 86.06(+) | 235 (+) | yes |
| 8 | 12 | 0.94 | 39,000 | 83.00(=) | 226 (+) | yes |
| 9 | 13 | 0.85 | 38,000 | 79.50(=) | 232 (+) | yes |
| 10 | 14 | 0.90 | 46,000 | 86.30(+) | 296 (+) | yes |
| | Control[17] | — | — | 76.00 | 331 | yes |

[18]95% C.L. = 95% confidence level using ANOVA and Tukey statistical tools, wherein (+) means that tested compisition was significantly different from the control composition and (=) means that the tested composition was essentially equivalent to the control composition.

The set retention test measures the ability of a hair spray composition to hold or retain a hair style for an extended time at a particular relative humidity. Set retention was measured by applying 0.5 cc (cubic centimeters) of the hair spray composition to a one gram hair tress, and testing six tresses per composition. The sprayed tresses were allowed to dry overnight, at 30% relative humidity (i.e., RH), in a zigzag shape. The tresses were hung inside a humidity chamber at 25° C. and a predetermined relative humidity (e.g., 70% RH). The relaxed length was recorded of the tresses and set retention was calculated using the equation:

$$\% \text{ Set Retention} = \frac{L - L_t}{L - L_o} \times 100,$$

wherein L is the length of the fully extended tress, $L_o$ is the length of sprayed hair before relaxation, $L_t$ is the length after exposure for a time, t. Six tresses were tested per hair spray composition and the data was statistically analyzed and compared at the 95% confidence level. In all the experiments, AMPHOMER was used as the resin in a control hair spray product.

Hair set retention was measured at 25° C. and a low relative humidity (i.e., 70% RH). Table 5 summarizes hair set retention tests, and hair crust tests, from hair spray compositions incorporating various carboxylated polyurethane resins listed in Table 1. The hair set retention and hair crust test results were compared to the results provided by a control hair spray product containing AMPHOMER. The comparative test shows that hair spray compositions containing a carboxylated polyurethane resin having an $M_w$ of greater than about 30,000 exhibited comparable or better set retention than AMPHOMER. The hair set retention provided by the carboxylated polyurethane resins, therefore, is considered to be excellent because AMPHOMER is used in successful commercial hair spray compositions.

The ability of the present hair spray composition to hold a hairstyle at high relative humidity (i.e., 85% RH) and 25° C. also were tested by the above-described method. The results are summarized in Table 6.

Hair crust also can be tested subjectively. In this test, a group of trained judges evaluated hair tresses sprayed with a hair spray composition containing a polyurethane resin or with the control composition. The data and test procedure are summarized in Table 6. Table 6 shows that overall the present hair spray compositions displayed comparable or lower crust within experimental error than the standard control composition.

TABLE 6

| Example | Polyurethane Resin | Stiffness and Crust[19] | Feel[20] | Flaking[21] | 1 hr. % Set Retention 1 hr. @ 85% RH[17] |
|---|---|---|---|---|---|
| 11 | 19 | 4.77 (+) | 5.02 (+) | 2.92 (+) | 65.43 |
| 12 | 20[5] | 4.28 (+) | 4.80 (+) | 3.75 (+) | 55.97 |
| 13 | 21 | 3.03 (+) | 2.68 (+) | 1.65 (+) | 46.07 (+) |
| 14 | 22[6] | 6.29 | 8.14 | 8.34 | 68.52 |
| 15 | 23[7] | 6.92 | 8.35 | 7.05 | 89.80 (+) |
| 16 | 24[8] | 8.29 (+) | 9.56 (+) | 8.43 | 91.40 (+) |
| 17 | 25 | 6.51 | 7.23 | 5.71 | 70.42 (+) |
| 18 | 26[9] | 4.50 (+) | 4.54 (+) | 1.82 (+) | 63.24 |
| 19 | 27 | 6.39 | 8.20 | 7.18 | 80.00 (+) |
| 20 | 28 | 5.53 | 6.51 (+) | 6.69 | 75.37 (+) |
| 21 | 29[10] | 4.21 (+) | 4.48 (+) | 4.22 (+) | 72.98 (+) |
| 22 | 30[11] | 4.88 (+) | 6.72 | 7.03 | 95.13 (+) |
|  | Control[16] | 7.00 | 7.00 | 6.00 | 62.50 |

[19]Two-inch wide, 6-inch long, 2 gram, clean hair tresses were treated with a hair spray composition. six tresses were tested for each composition. The tresses were allowed to dry and evaluated for stiffness and crust with the fingers by trained judges using a scale: 1 to 10 (1 = soft and natural, 10 very stiff);
[20]The evaluation protocol is similar to the one described in footnote 19 on a scale: 1 to 10 (= untreated hair, 10 = coated and glued hair): and
[21]The evaluation protocol is similar to the one described in footnote 19. However, instead of feeling the tresses, the tresses were combed and the amount and quality of the resin detached from the hair was visually evaluated by the trained judges.

The results summarized in Table 6 show that, except for Example 13, each of the hair spray compositions containing a carboxylated polyurethane resin having an $M_w$ at least 20,000, e.g., about 20,000 to about 70,000, performed as well as or better than the control hair spray product containing AMPHOMER. However, the composition of Example 13 imparted the desired properties of low stiffness, crust, and flaking, and a natural feel to treated hair tresses. The hair set retention provided by the carboxylated polyurethane resins, therefore, is considered to be superior because AMPHOMER is the resin used in successful commercial hair spray compositions.

Sprayed hair also was tested for hair crust, feel, and flaking. The hair crust test measures the hardness and/or stiffness of hair sprayed with a hair spray composition. Hair spray compositions that provide natural, or reduced, crusts are desired.

Hair crust can be tested by compression. In this test, two gram hair tresses were sprayed with one cubic centimeter of a hair spray composition. The sprayed tress then was rolled and set on a 2.4 centimeter (cm) diameter roller. Six tresses were tested for each hair spray composition. The rolled tresses were equilibrated overnight at 70% RH and 25° C. The tresses then were removed from the rollers and compressed to 25% strain using a Dia-Stron mini-tensile stress tester. The compression force was measured as gram force. The data was statistically analyzed and compared at the 95% confidence level. The results are summarized in Table 5.

The results in Table 5 show that a hair spray composition containing a carboxylated polyurethane resin exhibited lower compression forces than the control composition containing AMPHOMER. Hair sprayed with the compositions of Examples 1–10, therefore, had lower crust and better feel than hair sprayed with the control composition. Accordingly, the present hair spray compositions outperformed the control composition in the hair crust test.

Table 6 also summarizes data and the test procedure for hair feel. The data in Table 6 shows that a hair spray composition containing a carboxylated polyurethane resin having an $M_w$ of below 65,000, e.g., about 20,000 to about 65,000, imparted better hand feel properties to sprayed hair than the control composition. It also was found that hand feel properties of sprayed hair was maximized for hair spray compositions containing a carboxylated polyurethane resin having an $M_w$ of less than about 40,000, e.g., about 20,000 to about 40,000, and an R-value below about 0.75, i.e., about 0.40 to about 0.75.

Hair sprayed with the hair spray compositions also were tested for the amount of flakes or dust that form on the hair after combing hair that has been sprayed with the composition and dried. Table 6 shows that, in general, hair spray compositions containing a carboxylated polyurethane resin performed equally to the control composition. In particular, hair spray compositions containing a carboxylated polyurethane resin having an $M_w$ of less than about 40,000 and an R-value of less than 0.75 outperformed the control composition.

Many modifications and variations of the invention as hereinbefore set forth can be made without departing from the spirit and scope thereof, and, therefore, only such limitations should be imposed as are indicated by the appended claims.

What is claimed is:

1. A method of treating hair to fix the hair in a desired hairstyle consisting essentially of:
   (a) configuring the hair in the desired hairstyle; and
   (b) applying a hair spray composition to the hair, said hair spray composition consists essentially of
      (i) about 0.25% to about 6% by weight of a carboxylated polyurethane resin;
      (ii) 0% to about 80% by weight of an alcohol; and (iii) about 15% to about 95% by weight water, wherein the carboxylated polyurethane resin has a weight average molecular weight of about 15,000 to about 150,000, an acid value of about 7 mg to about 50 mg KOH per g resin, a melting point of about 40 C. to about 120 C. and is a reaction product of a mixture comprising:
 (A) about 10% to about 90% by weight of the mixture of a polyoxyalkylene diol having a number average molecular weight of about 400 to about 20,000;
 (B) about 0.01% to about 20% by weight of the mixture of an alkylene glycol;
 (C) about 3% to about 80% by weight of the mixture of an organic diisocyanate;
 (D) about 0.1% to about 30% by weight of the mixture of a 2,2-di(hydroxymethyl)alkanoic acid; and
 (E) about 0.001% to about 0.95% by weight of the mixture of water, wherein a ratio of isocyanate groups to hydroxyl groups is about 0.4 to about 1.1.

2. The method of claim 1 wherein the hair spray composition further comprises about 5% to about 30% by weight of a propellant.

3. The method of claim 1 wherein the hair is configured in the desired hairstyle prior to applying the hair spray composition.

4. The method of claim 1 wherein the hair is configured in the desired hairstyle after applying the hair spray composition.

5. The method of claim 4 wherein the hair is configured using a curling iron or a blow dryer.

* * * * *